(12) United States Patent
Safar et al.

(10) Patent No.: US 11,747,315 B2
(45) Date of Patent: Sep. 5, 2023

(54) FLARE SYSTEM HEATING VALUE MONITORING METER

(71) Applicant: Saudi Arabian Oil Company, Dhahran (SA)

(72) Inventors: Anas H. Safar, Dhahran (SA); Mohammed A. Al-Mahmood, Dhahran (SA); Yousef D. Aloufi, Dhahran (SA); Abdullmajeed I. Al Sanad, Dhahran (SA); Mohammed A. Aljallal, Dammam (SA)

(73) Assignee: Saudi Arabian Oil Company, Dhahran (SA)

( * ) Notice: Subject to any disclaimer, the term of this patent is extended or adjusted under 35 U.S.C. 154(b) by 26 days.

(21) Appl. No.: 17/487,446

(22) Filed: Sep. 28, 2021

(65) Prior Publication Data
US 2023/0096405 A1    Mar. 30, 2023

(51) Int. Cl.
*G01N 33/00*     (2006.01)
*H04L 67/12*     (2022.01)

(52) U.S. Cl.
CPC .......... *G01N 33/0073* (2013.01); *H04L 67/12* (2013.01)

(58) Field of Classification Search
CPC ............................ G01N 33/0073; H04L 67/12
See application file for complete search history.

(56) References Cited

U.S. PATENT DOCUMENTS

| 4,202,168 A | 5/1980 | Acheson et al. |
| 8,967,995 B1 | 3/2015 | Griffin et al. |
| 10,029,291 B2 | 7/2018 | Fischer et al. |
| 2003/0069743 A1 | 4/2003 | Nordrum |
| 2010/0070404 A1 | 3/2010 | McConnell |
| 2014/0266740 A1 | 9/2014 | Fernandes et al. |

(Continued)

FOREIGN PATENT DOCUMENTS

| EP | 2309186 | 4/2011 |
| EP | 2330347 | 6/2011 |

OTHER PUBLICATIONS

PCT International Search Report and Written Opinion in International Appln. No. PCT/US2022/077028, dated Jan. 23, 2023, 12 pages.

(Continued)

*Primary Examiner* — Manuel A Rivera Vargas
(74) *Attorney, Agent, or Firm* — Fish & Richardson P.C.

(57) ABSTRACT

Systems and methods include a computer-implemented method for providing flare header information. Instantaneous flaring flowrate data is received from flaring sources of a flare network of a processing facility. The instantaneous flaring flowrate data is analyzed in conjunction with physical properties of relief sources obtained from a heat and material balance of the processing facility. A heating value and a molecular weight are determined for each relief source and flare header using a processing model associated with a relief source type, size, and identifications. The relief sources are connected using a data signal received and processed using the processing model. Reports are generated showing average daily heating values and molecular weights for each flare header. A real-time display is provided for monitoring instantaneous heating values and molecular weights for each flare header on a real-time basis.

20 Claims, 9 Drawing Sheets

(56) References Cited

U.S. PATENT DOCUMENTS

| | | | |
|---|---|---|---|
| 2015/0260397 A1* | 9/2015 | Talasila | F23N 5/022 431/14 |
| 2017/0370579 A1 | 12/2017 | Johnson et al. | |
| 2019/0242575 A1* | 8/2019 | Fisher | F23L 7/005 |
| 2019/0366400 A1 | 12/2019 | Chambers et al. | |
| 2021/0372864 A1 | 12/2021 | Tao et al. | |
| 2023/0128460 A1 | 4/2023 | Safar et al. | |

OTHER PUBLICATIONS

U.S. Appl. No. 17/486,004, Safar et al., filed Sep. 27, 2021.
Engineering Data Book, The Gas Processor Suppliers Association (GPSA), 12th Edition, vol. 1, Chapter 5: Relief Systems, 2004, 25 pages.
Sick, "Flowsic100 Flare: Reliable gas flow measurement in flare gas applications," Oct. 2021, retrieved Jul. 13, 2022, retrieved from URL <https://www.bakerhughesds.com/panametrics/sensors-probes-transducers-transmitters/oil-and-gas/panametrics-flare>, 5 pages.
bakerhughesds.com [online], "Flare gas measurement & control solutions," 2021, retrieved Aug. 9, 2021 from URL<https://www.bakerhughesds.com/panametrics/flare-management>, 11 pages.
Boneu et al., "How and when to monitor a patient treated with low molecular weight Heparin," Seminars in Thrombosis and Hemostasis, Oct. 2001, 27(5):519-522, 4 pages.
Compendium of Greenhouse Gas Emissions Methodologies for the Oil and Natural Gas Industry, American Petroleum Institute, Aug. 2009, 807 pages.
Eddleman et al., "Flare monitoring regulatory compliance and analyzers: An analysis," Yokogawa, 2018, 4 pages.
Gilmer et al., "Draft flare waste gas flow rate and composition measurement methodologies evaluation document," Texas Commission on Environmental Quality, Work Assignment 5, Shell Global Solutions, available on or before Jun. 2013 via Internet Archive Wayback Machine URL <https://web.archive.org/web/20131101000000*/https://www.tceq.texas.gov/assets/public/implementation/air/am/contracts/reports/oth/FLARE_WASTE_GAS_FLOW_RATE.pdf>, 141 pages.
Mandatory Greenhouse Gas Reporting, 40 CFR § 98, Chapter I, Subchapter C, Oct. 2009, 581 pages.
Moorman et al., "Lower heating value sensor for fuel monitoring," IEEE Sensors, 2005, 802-805.
sick.com [online], "Gas flow measuring instruments FLOWSIC100 Flare," 2021, retrieved Aug. 9, 2021 from URL<https://www.sick.com/th/en/flow-measurement-technology/gas-flow-measuring-instruments/flowsic100-flare/c/g198253>, 7 pages.
thermofisher.com [online], "Flare stack emission monitoring," Available on or before May 4, 2021, via Internet Archive Wayback Machine URL <https://web.archive.org/web/20210420073913/https://www.thermofisher.com/us/en/home/industrial/manufacturing-processing/flare-stack-emission-monitoring.html>, retrieved on Oct. 12, 2021, retrieved from URL <https://www.thermofisher.com/sa/en/home/industrial/manufacturing-processing/flare-stack-emission-monitoring.html>, 4 pages.
Zeng et al., "Validation of a new method for measuring and continuously monitoring the efficiency of industrial flares," Journal of the Air & Waste Management Association, 2016, 66(1):76-86, 12 pages.
Umukoro et al., "Modelling emissions from natural gas flaring," Journal of King Saud University—Engineering Sciences, 2017, 29:178-182, 5 pages.
PCT International Search Report and Written Opinion in International Appln. No. PCT/US2022/077030, dated Jan. 30, 2023, 14 pages.
PCT International Search Report and Written Opinion in International Appln. No. PCT/US2022/078596, dated Feb. 2, 2023, 15 pages.

* cited by examiner

FLARE SYSTEM HEATING VALUE MONITORING METER

TECHNICAL FIELD

The present disclosure applies to monitoring and controlling flare systems.

BACKGROUND

Flare systems include gas flares (or flare stacks) that provide gas combustion at industrial plants such as at onshore and offshore oil and gas production sites. Flare systems can provide venting during start-up or shut-down, and can handle emergency releases from safety valves, blow-down, and de-pressuring systems.

SUMMARY

The present disclosure describes techniques that can be used for monitoring and controlling flare systems. In some implementations, a computer-implemented method includes the following. Instantaneous flaring flowrate data is received from flaring sources of a flare network of a processing facility. The instantaneous flaring flowrate data is analyzed in conjunction with physical properties of relief sources obtained from a heat and material balance of the processing facility. A heating value and a molecular weight are determined for each relief source and flare header using a processing model associated with a relief source type, size, and identifications. The relief sources are connected using a data signal received and processed using the processing model. Reports are generated showing average daily heating values and molecular weights for each flare header. A real-time display is provided for monitoring instantaneous heating values and molecular weights for each flare header on a real-time basis.

The previously described implementation is implementable using a computer-implemented method; a non-transitory, computer-readable medium storing computer-readable instructions to perform the computer-implemented method; and a computer-implemented system including a computer memory interoperably coupled with a hardware processor configured to perform the computer-implemented method, the instructions stored on the non-transitory, computer-readable medium.

The subject matter described in this specification can be implemented in particular implementations, so as to realize one or more of the following advantages. The flare monitoring and controlling system can aid operators in reducing, for example, supplement cover gas that is added in acid gas flare systems. This can occur when the flared gas heating value is below a minimum design requirement or below a minimum standard requirement of a company running the system. Reducing supplement cover gas can lead to a significant reduction in intermittent purge gas used as a supplement. The flare monitoring and controlling system can also help a plant in reducing their emissions by improving the combustion efficiency of flare gas. Knowledge of instantaneous heating values of flared gas can help operators to control assist gas and air to achieve smokeless operations, which can then lead to minimizing emissions. Since every flare tip is designed for a minimum heating value in order for it operate within its smokeless capacity, knowing the heating value can allow operators to meet the design requirement and hence improve the reliability of the flare tip. In addition, real-time molecular weight results can aid operators in minimizing the downtime of flow maters and in improving the emissions calculation accuracy. This can help to measure and monitor the heating value of each flare header and the molecular weight which will help in: reducing combustible fluid losses (or de-carbonization), reducing emissions by improving combustion efficiency, enhancing flare tip reliability, calibrating flow meters, and improving the accuracy of greenhouse gas (GHG) emission calculations. The techniques of the present disclosure can compute heating values based on data from individual flaring sources. This provides a higher accuracy as compared to utilizing composition at the end of the header, as done by conventional systems, which may have a limitation on measuring ranges and may require frequent calibration and maintenance. The techniques of the present disclosure have no limitations in reading range and require no maintenance, ensuring accurate results at all times and avoiding uncertainties in the readings. No costly devices are required to be installed at a facility.

The details of one or more implementations of the subject matter of this specification are set forth in the Detailed Description, the accompanying drawings, and the claims. Other features, aspects, and advantages of the subject matter will become apparent from the Detailed Description, the claims, and the accompanying drawings.

DESCRIPTION OF DRAWINGS

Like reference numbers and designations in the various drawings indicate like elements.

DETAILED DESCRIPTION

The following detailed description describes techniques for monitoring and controlling flare systems. Various modifications, alterations, and permutations of the disclosed implementations can be made and will be readily apparent to those of ordinary skill in the art, and the general principles defined may be applied to other implementations and applications, without departing from scope of the disclosure. In some instances, details unnecessary to obtain an understanding of the described subject matter may be omitted so as to not obscure one or more described implementations with unnecessary detail and inasmuch as such details are within the skill of one of ordinary skill in the art. The present disclosure is not intended to be limited to the described or illustrated implementations, but to be accorded the widest scope consistent with the described principles and features.

A flare system heating value monitoring system can be used as a solution that provides the capability to compute actual heating values (for example, heat of combustion) and molecular weights of flared gas for each header of a flare network. The system can receive instantaneous flaring flowrate data from a processing facility's flaring sources and can analyze the data in conjunction with the heat and material balance of the processing facility. The data can then be used to perform a comprehensive heating value and molecular weight calculation for each flare header throughout the flare network.

The results of the analysis can be provided to operators in the form of reports that show average daily heating values and molecular weights for each flare header. A user interface can provide a real-time display to monitor instantaneous heating values and molecular weights for each flare header. This solution can aid operators in monitoring the flare gas heating value and molecular weights in real-time and can help in maintaining required minimum heating values. The term real-time can correspond to events that occur within a specified period of time, for example, within a few seconds or a few minutes.

The system can also aid in optimizing supplement assist gas that is added to a network when the flare gas heating value is below a design value. The system can also help in enhancing the smokeless operation of flare systems by overcoming the challenge of the dynamic changes in compositions.

In some implementations, utilizing volumetric flowrate of each relief source by a flare network monitoring system can include the following. A flare monitoring system can receive real-time data associated with the release of a processing facility's combustible fluids to a flare stack. The data can be analyzed in conjunction with parameters of the processing facility's flare-through elements such as manual valves, control valves, restriction orifices, flow meters, and the like. The results of the analysis can be provided to operators in the form of reports that indicate: whether flaring events are of a routine or non-routine nature; the flared volume; the contribution of the flare-through elements to the flared volume; and so forth. The results can aid operators in reducing combustible fluid losses due to flaring and in mitigating emissions of sulfur, nitrogen and carbon dioxide.

The discharge composition of each relief source connected to the flare network can be used, for example, in calculating corresponding heating values and molecular weights of each relief device:

$$HHV_{d1} = \Sigma_{i=1}^{n}(Xi_1 \times HHV_1 \times Xi_2 \times HHV_2 \ldots) \quad (1)$$

$$LHV_{d1} = \Sigma_{i=1}^{n}(Xi_1 \times LHV_1 + Xi_2 \times LHV_2 \ldots) \quad (2)$$

$$MW_{d1} = \Sigma_{i=1}^{n}(Xi_1 \times MW_1 + Xi_2 \times MW_2 \ldots) \quad (3)$$

where $HHV_{d1}$ is a higher heating value of relief device 1 (for example, in standard cubic feet (scf) per British thermal unit (scf/btu)); $LHV_{d1}$ is a lower heating value of relief device 1 (for example, in scf/btu); $MW_{d1}$ is the molecular weight of relief device 1 (for example, in pounds per pound-mole (lb/lb-mol)); $X_i$ is a mole fraction of the component i; $HHV_i$ is a higher heating value of component i (for example, in scf/btu); $LHV_i$ is a lower heating value of component i (for example, in scf/btu); and $MW_i$ is the molecular weight of component i (for example, in lb/lb-mol).

Calculating the corresponding heating values and molecular weight of each flare header yields:

$$HHV_{h1} = \Sigma_{i=1}^{n}(Xi_1 \times HHV_1 \times Xi_2 \times HHV_2 \ldots) \quad (4)$$

$$LHV_{h1} = \Sigma_{i=1}^{n}(Xi_1 \times LHV_1 + Xi_2 \times LHV_2 \ldots) \quad (5)$$

$$MW_{h1} = \Sigma_{i=1}^{n}(Xi_1 \times MW_1 + Xi_2 \times MW_2 \ldots) \quad (6)$$

where $HHV_{h1}$ is a higher heating value of flare header 1 (for example, in scf/btu); and $LHV_{h1}$ is a lower heating value of flare header 1 (for example, in scf/btu); $MW_{h1}$ is the molecular weight of flare header 1 (for example, in lb/lb-mol); $X_i$ is the mole fraction of the component i; $HHV_i$ is the higher heating value of component i (for example, in scf/btu); $LHV_i$ is the lower heating value of component i (for example, in scf/btu); and $MW_i$ is the molecular weight of component i (for example, in lb/lb-mol).

Performance equation (for example, a performance index (PI) expiration) can be developed using Equations (1) to (6) to create PI tags on a PI server. The PI tags can be used in a real-time display of a facility, for example, in a monitoring dashboard used to illustrate and monitor actual flaring compositions.

Figure 1:
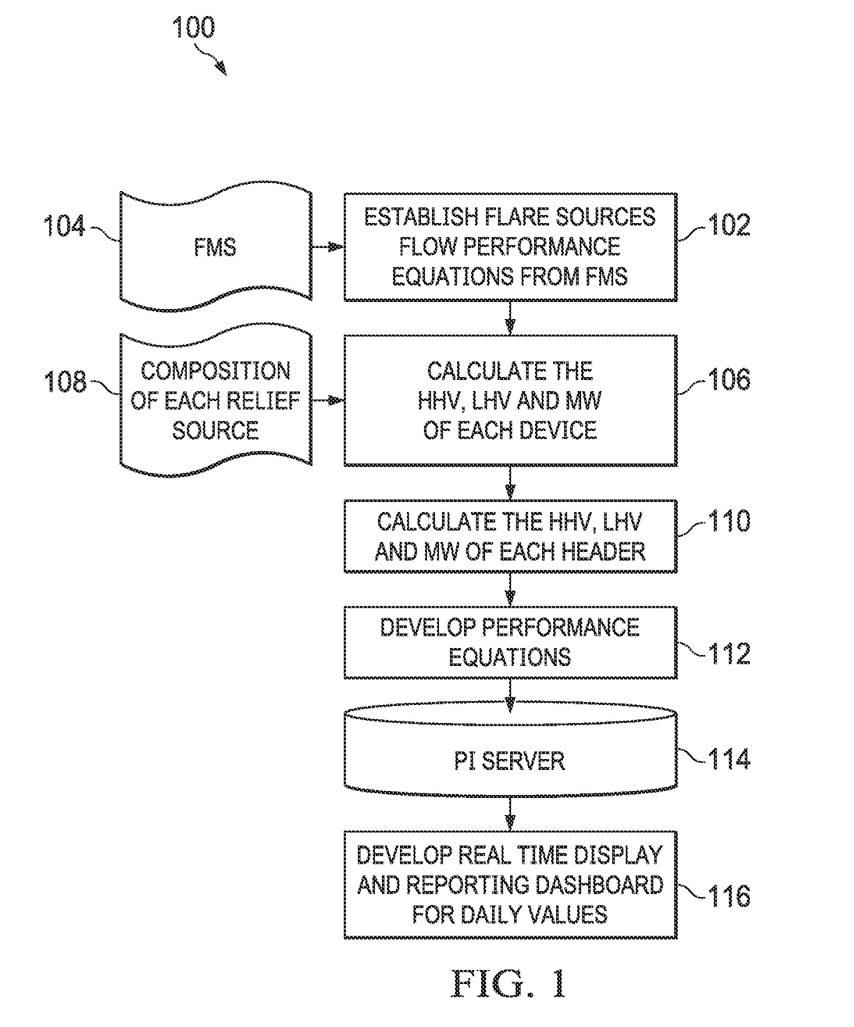
FIG. 1 is a flow diagram showing an example of a workflow for generating a real-time display for a flare monitoring system, according to some implementations of the present disclosure.

FIG. 1 is a flow diagram showing an example of a workflow 100 for generating a real-time display for a flare monitoring system, according to some implementations of the present disclosure. At 102, flare sources flow performance equations are established by a flare monitoring system (FMS) 104. At 106, the compositions 108 of each relief source are used to calculate HHV, LHV, and MW values for each device. At 110, HEW, LHV, and MW values are calculated for each header. At 112, performance equations are developed for each component and stored on a PI server 114. At 116, a real-time display and reporting dashboard is developed, using the PI server 114, to display daily values.

Figure 2:
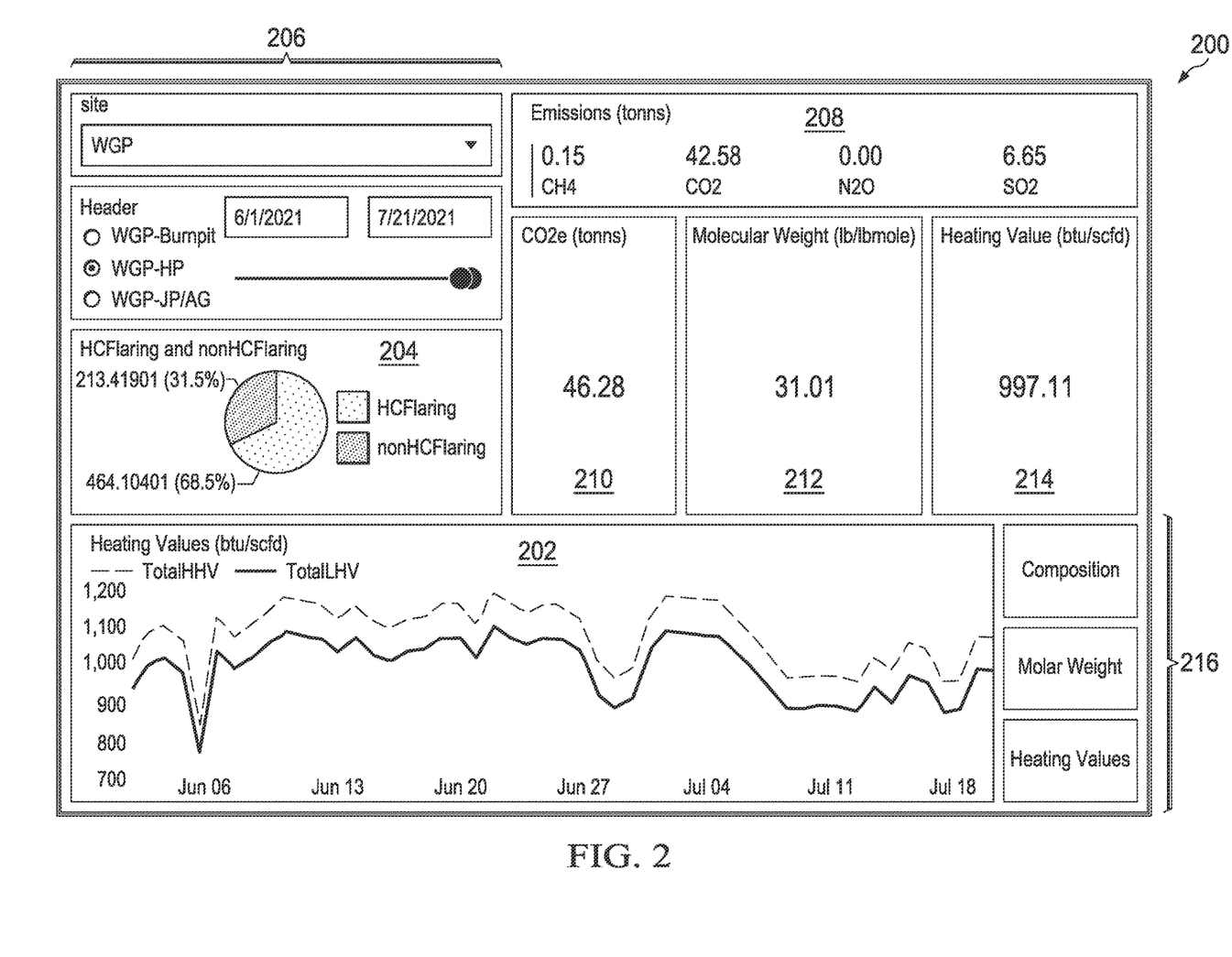
FIG. 2 is a screenshot showing an example of a user interface for displaying composition information, according to some implementations of the present disclosure.

FIG. 2 is a screenshot showing an example of a user interface 200 for displaying composition information, according to some implementations of the present disclosure. The user interface 200 includes a graph area 202 which demonstrates a daily trend of the lower and higher heating value of the flared hydrocarbon. An area 204 includes a display of hydrocarbon flaring and non-hydrocarbon flaring volumes. An area 206 illustrates a dropdown list of operating facilities that the user can select to view the results. The dropdown list is based on mapping each individual operating facility with a unique site ID in the data base.

An area 208 displays information that demonstrates the cumulative values of emissions for the selected operating facility, header, and time frame. The emissions include methane, carbon dioxide, nitrogen oxide, and sulfur dioxide. An area 210 shows an average value of a carbon dioxide equivalent attributed to flaring for the selected operating facility and timeframe. An area 212 this shows an average value of molecular weight attributed to flaring for the selected operating facility and timeframe. An area 214 shows an average value of heating value attributed to flaring for the selected operating facility and timeframe. An area 216 includes navigation buttons from which users can display daily trends of the selected parameters including the flaring molecular weight and heating value.

Figure 3:
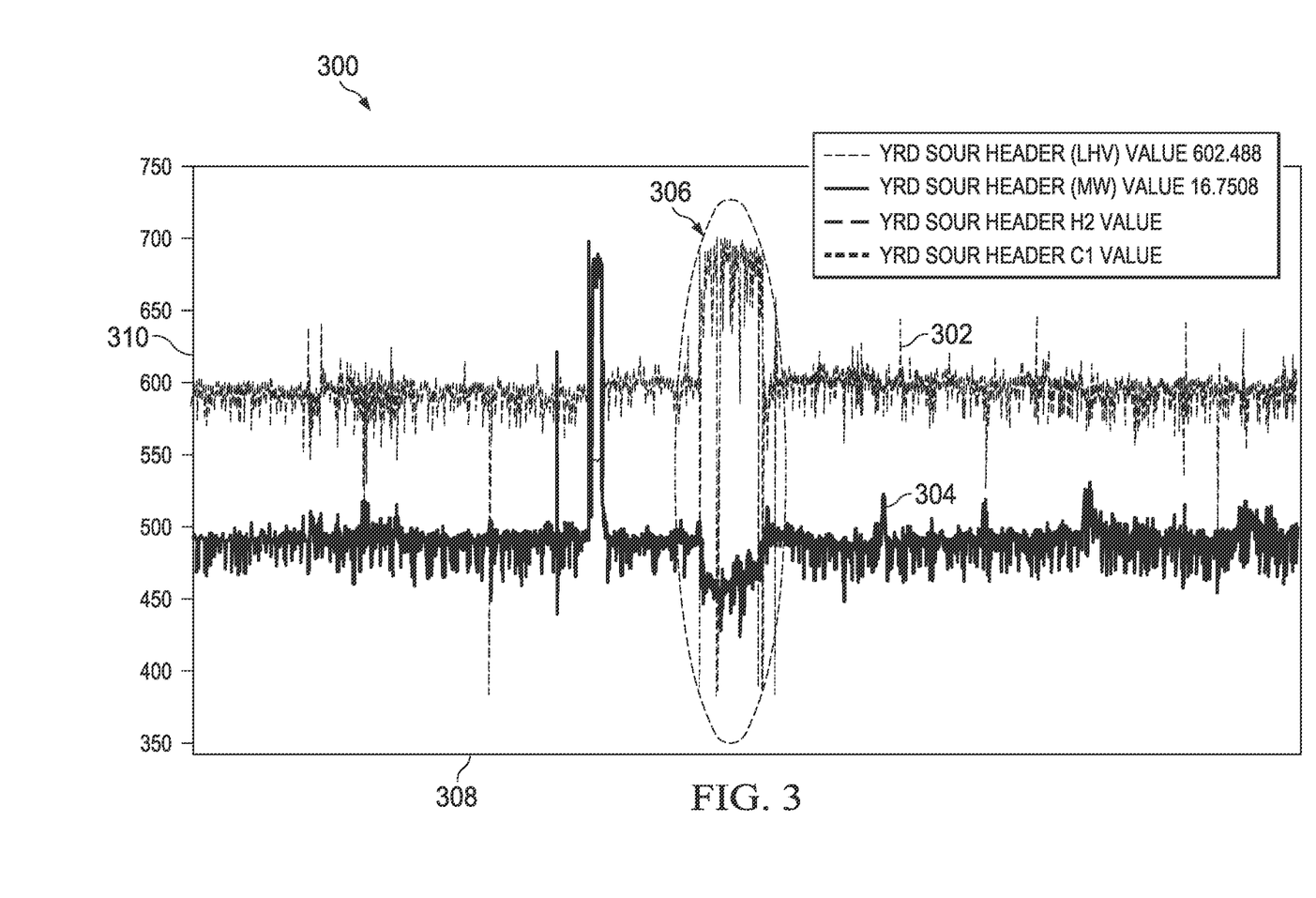
FIG. 3 is a graph showing example sour header values over time, according to some implementations of the present disclosure.

FIG. 3 is a graph 300 showing example sour header values over time, according to some implementations of the present disclosure. For example, the graph 300 shows real-time trends of the heating value 302 and molecular weight 304. Region 306 on the graph 300 shows a time period during which the heating value of the flared gasses has elevated, indicating that a flaring source with higher hydrocarbon content was flowing into the flare system. Region 306 on the graph 300 also shows the molecular weight was reduced during the flaring event which indicated the properties of the relief sources that caused flaring.

Figure 4A:
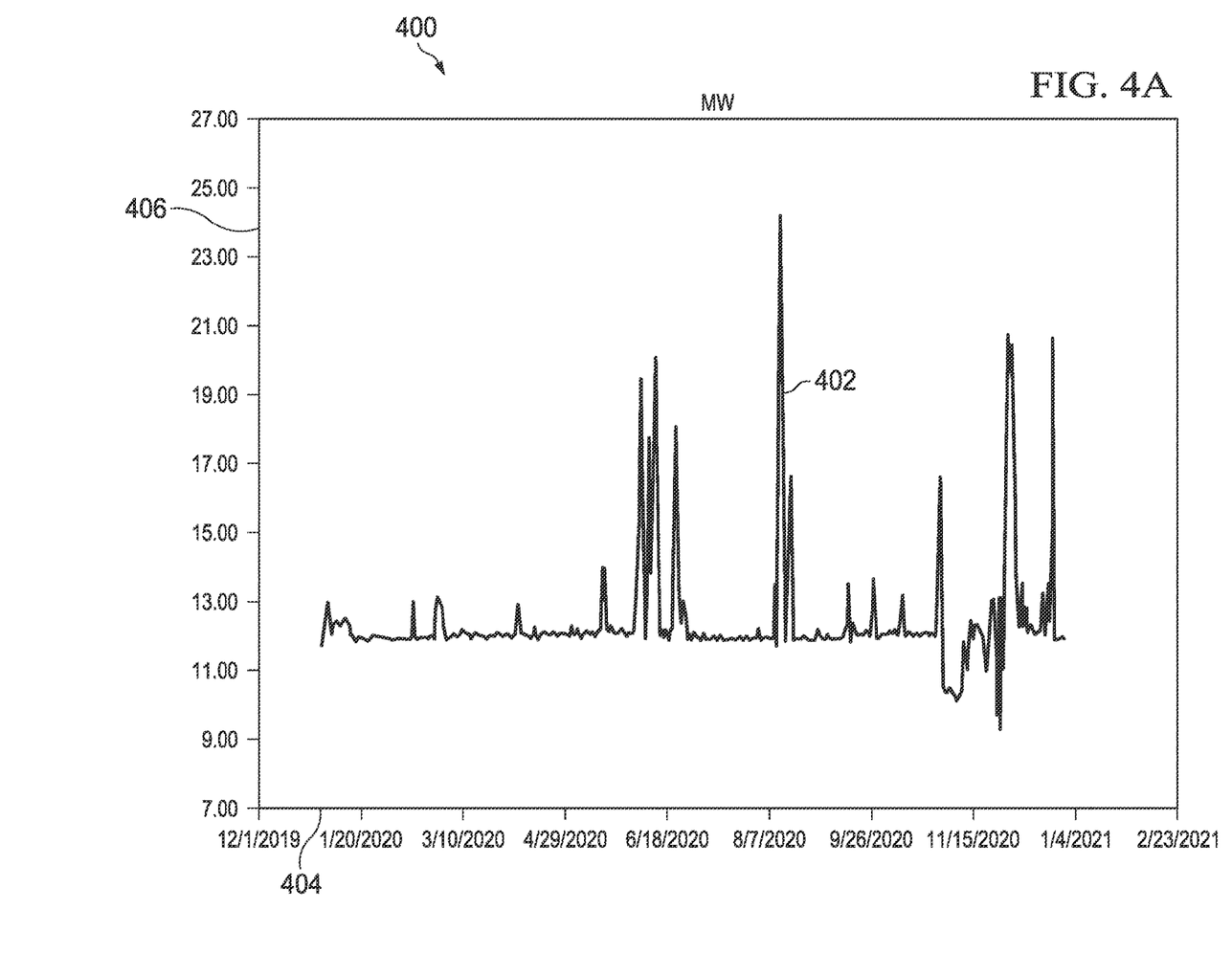
FIGS. 4A and 4B are graphs showing examples of a molecular weight (MW) plot and a heating value plot.
Figure 4B:
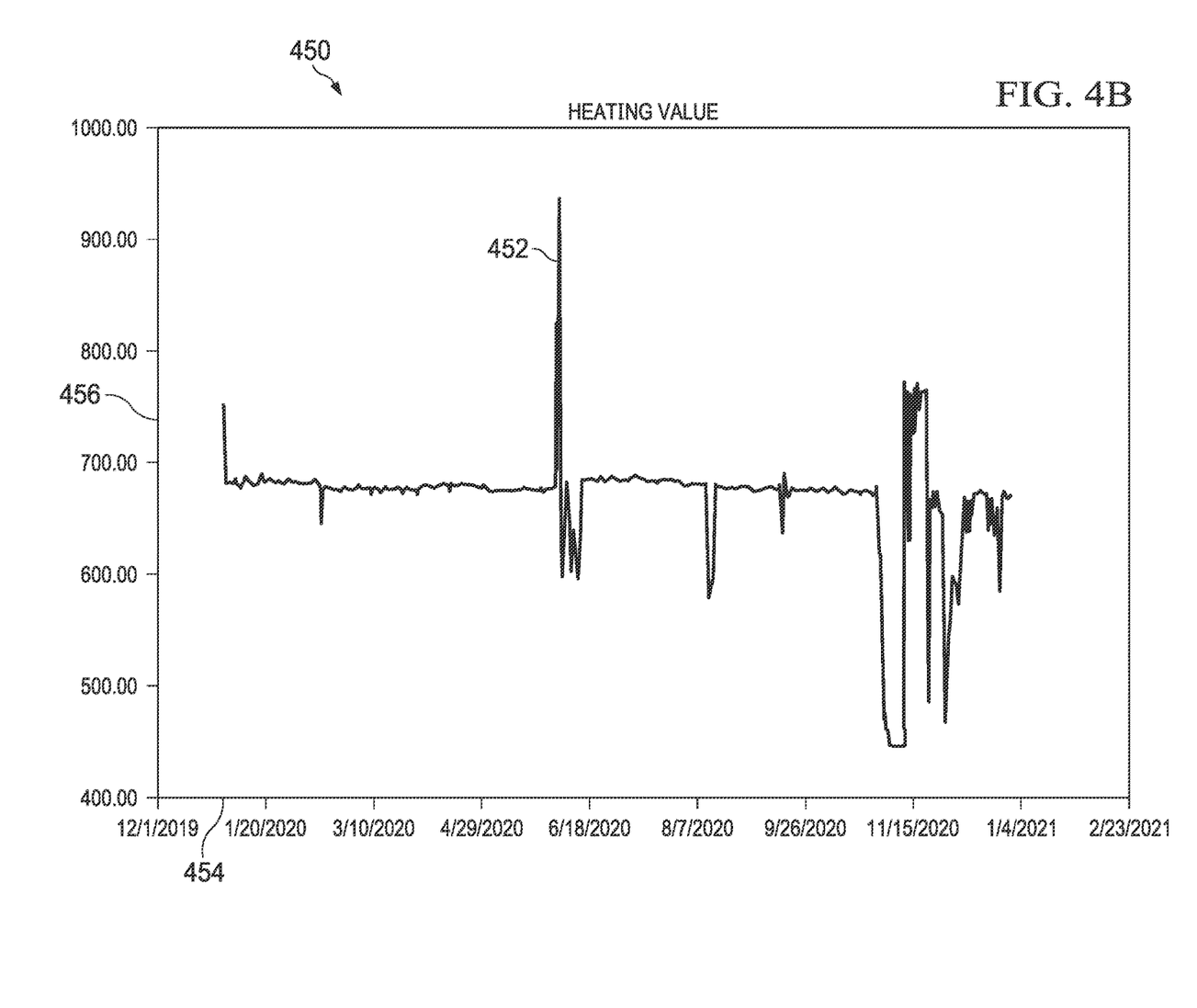

FIGS. 4A and 4B are graphs 400, 450 showing examples of a molecular weight (MW) plot 402 and a heating value plot 452. The MW plot is plotted relative to a time axis 404 and a MW axis 406. The heating value plot 452 is plotted relative to a time axis 454 and a heating value axis 456. Graphs 400 and 450 demonstrate that the molecular weight and heating value of the flared gasses fluctuates based on the sources of the flaring events which is computed by implementations of the present disclosure.

Figure 5:
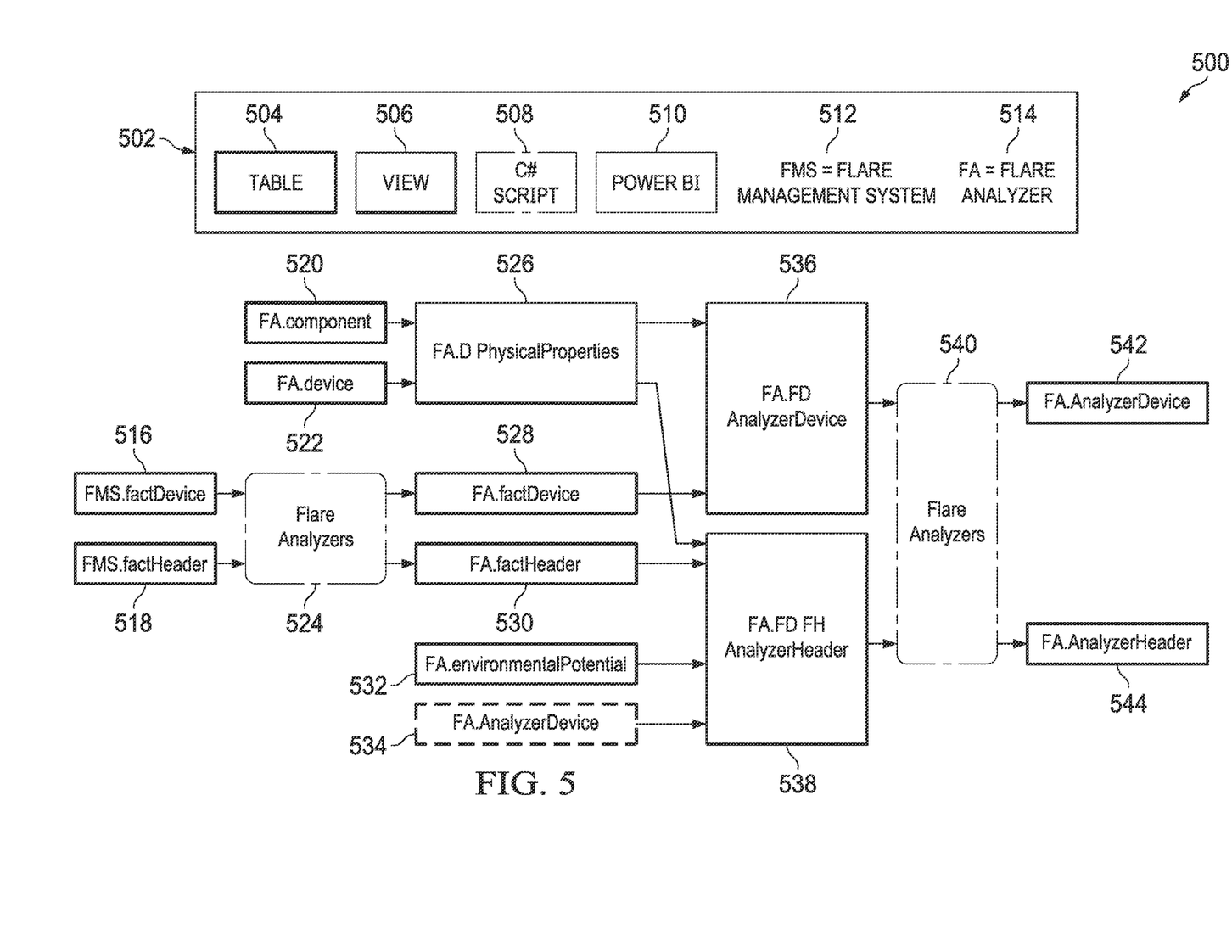
FIG. 5 is a block diagram showing an example of a system data flow for flare analysis, according to some implementations of the present disclosure.

FIG. 5 is a block diagram showing an example of a system data flow 500 for flare analysis, according to some implementations of the present disclosure. A key 502 shows line styles for elements of the system data flow 500, including tables 504, views 506, C# scripts 508, and business intelligence (BI) units 510 for elements related to flare analyzers (FA) 512 and flare monitoring systems (FMS) 514. Elements of the system data flow 500 include FMS.factDevice table 516, FMS.factHeader table 518, FA.component table 520; FA.device table 522, flare analyzer script(s) 524, FA.D_PhysicalProperties view 526; FA.factDevice table 528, FA.factHeader table 530, FA.environmentalPotential table 532, FA.AnalyzerDevice table 534, FA.FD_AnalyzerDevice view 536, FA.FD_FH_AnalyzerHeader view 538, flare analyzer script(s) 540, FA.AnalyzerDevice table 542, and FA.AnalyzerHeader table 544.

Figure 6:
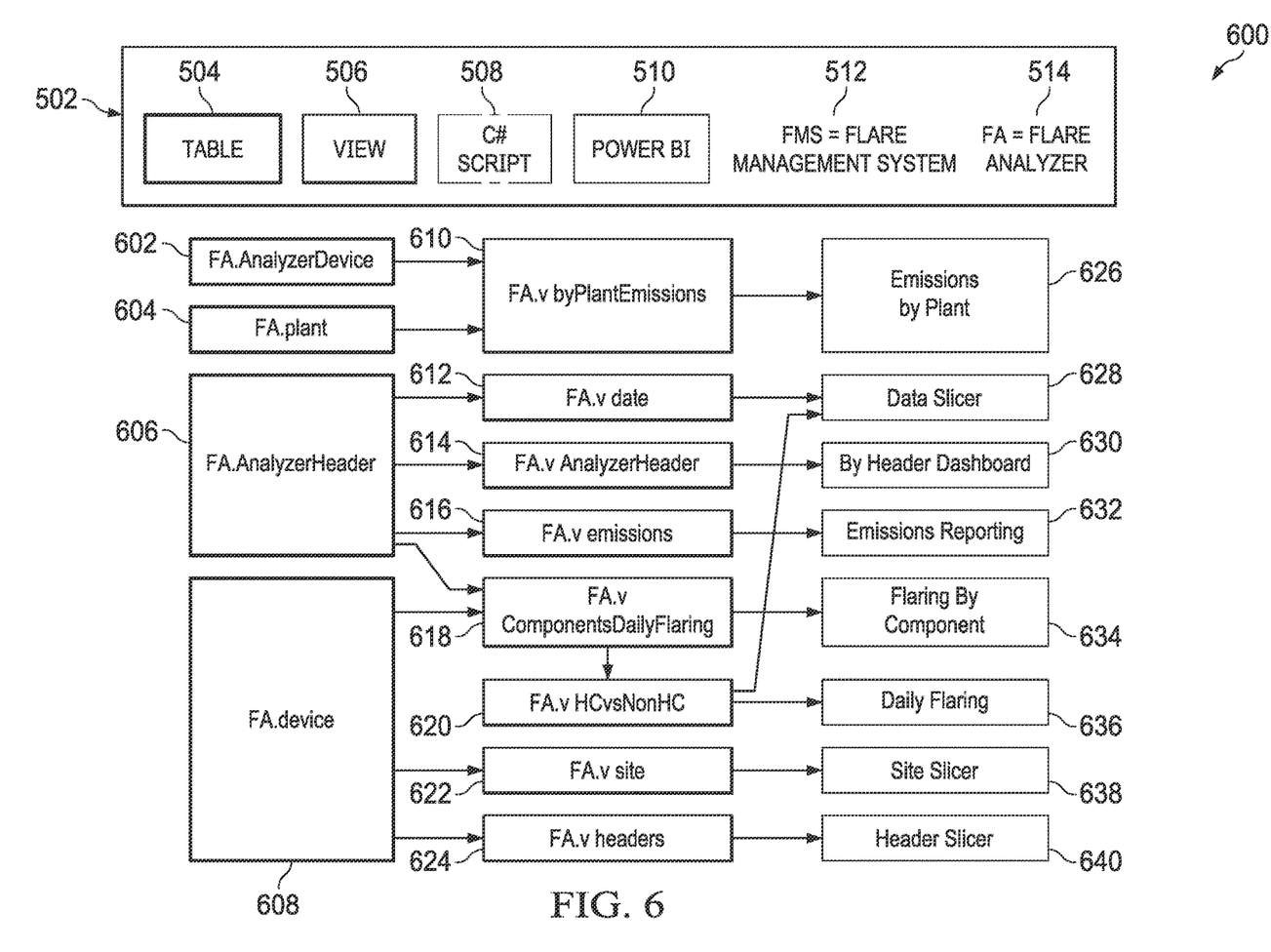
FIG. 6 is a block diagram showing an example of a system data flow for flare analysis, according to some implementations of the present disclosure.

FIG. 6 is a block diagram showing an example of a system data flow 600 for flare analysis, according to some implementations of the present disclosure. The system data flow 600 includes some of the same elements and types of elements as the system data flow 500 of FIG. 5. Together, data flows 500 and 600 are used for flare analysis. The system data flow 600 includes FA.AnalyzerDevice table 602, FA.plant table 604, FA.AnalyzerHeader table 606, FA.device table 608, FA.v_byPlantEmissions 610, FA.v_date view 612, FA.v_AnalyzerHeader view 614, FA.v_emissions view 616, FA.v_ComponentsDailyFlaring view 618, FA.v_HCvsNonHC view 620, FA.v_site, view 622 FA.v_headers view 624, Emissions by Plant BI 626, Date Slicer BI 628, By Header Dashboard BI 630, Emissions Reporting BI 632, Flaring by Component BI 634, Daily Flaring BI 636, Site Slicer BI 638, and Header Slicer BI 640.

The resulting two tables from FIG. 5, FA.AnalyzerDevice table 542 and FA.AnalyzerHeader table 544 can be used as the main data sources for the POWER BI elements, including Emissions by Plant 626, Date Slicer 628, By Header Dashboard 630, Emissions Reporting 632, Flaring by Component 634. and Daily Flaring 636.

Figure 7:
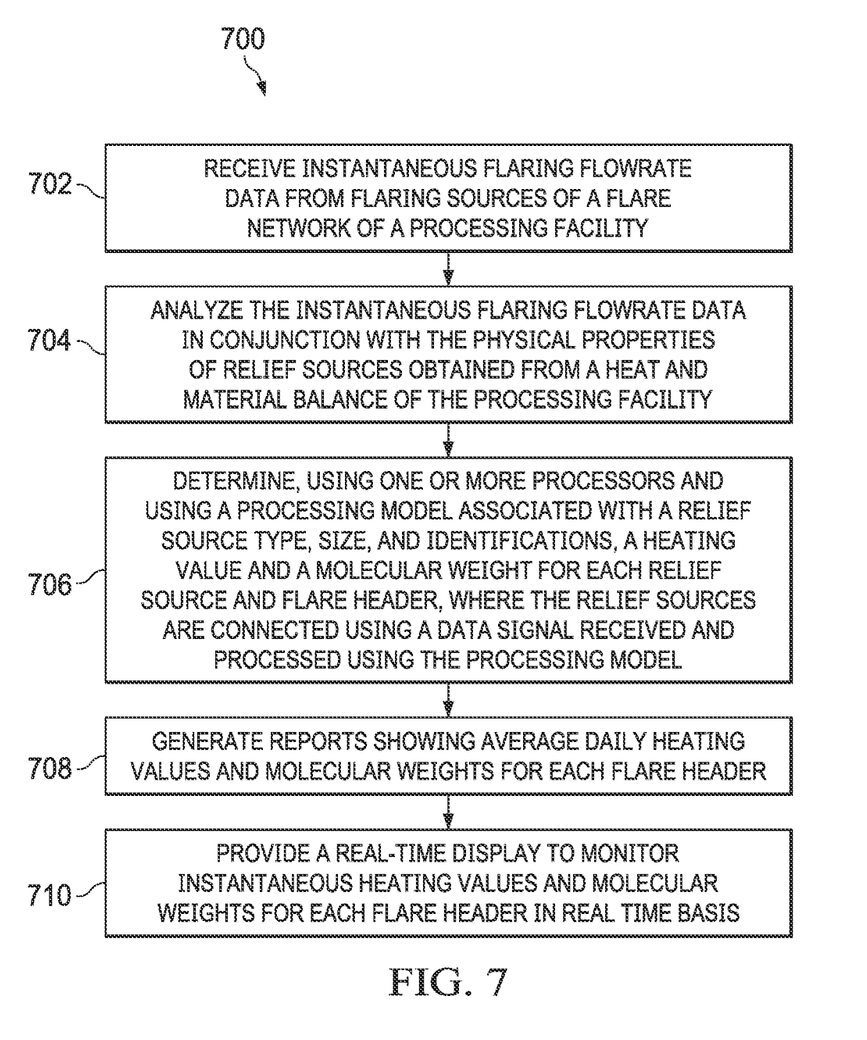
FIG. 7 is a flowchart of an example of a method for generating a real-time display to monitor instantaneous heating values and molecular weights for flare headers, according to some implementations of the present disclosure.

FIG. 7 is a flowchart of an example of a method 700 for generating a real-time display to monitor instantaneous heating values and molecular weights for flare headers, according to some implementations of the present disclosure. For clarity of presentation, the description that follows generally describes method 700 in the context of the other figures in this description. However, it will be understood that method 700 can be performed, for example, by any suitable system, environment, software, and hardware, or a combination of systems, environments, software, and hardware, as appropriate. In some implementations, various steps of method 700 can be run in parallel, in combination, in loops, or in any order.

At 702, instantaneous flaring flowrate data is received from flaring sources of a flare network of a processing facility. For example, flaring data can be received from an onshore or offshore oil or gas production site or refinery. From 702, method 700 proceeds to 704.

At 704, the instantaneous flaring flowrate data is analyzed in conjunction with the physical properties of a relief source using a heat and material balance of the processing facility. For example, analyzing the instantaneous flaring flowrate data includes using a data flow network of tables, views, scripts, and power business intelligence (BI) elements, as described with reference to FIGS. 5 and 6. The data flow network of tables, views, and scripts can further be stored in a data historian model operable to store into memory: parameters of flare-through elements concerning a relationship between generated data signals and a quantitative heating value and a molecular weight at each relief source; data associated with a heating value and a molecular weight of the flare header; and data associated with a heating value and a molecular weight for each plant. From 704, method 700 proceeds to 706.

At 706, a heating value and a molecular weight for each relief source and flare header are determined using one or more processors and using a processing model associated with a relief source type, size, and identifications. This can be part of performing a comprehensive heating value and molecular weight calculation for each flare header throughout the flare network. The relief sources can be connected using a data signal received and processed using the processing model. As an example, graphs 400 and 450 can be generated that display the MW plot 402 and the heating value plot 452, respectively. The calculations can be based on Equations (1) to (6), for example. From 706, method 700 proceeds to 708.

At 708, reports are generated showing average daily heating values and molecular weights for each flare header. As an example, generating reports can include identifying whether particular flaring events are of a routine or non-routine nature, a flared volume, and a contribution of the flare-through elements to the flared volume. The reports can be accessible from within a user interface, such as described with reference to FIG. 2. From 708, method 700 proceeds to 710.

At 710, a real-time display is provided to monitor instantaneous heating values and molecular weights for each flare header in real time basis. For example, providing the real-time display can include displaying, for each flare header, heating values over time. In another example, the real-time display can include displaying molecular weights and a heating value. In another example, providing the real-time display can include displaying, for each flare header, a graph showing significant fluctuations in reading relative to a time period. After 710, method 700 can stop.

Pilot experiments were run on a refinery using techniques of the present disclosure. Unexpected (high) heating values of flared gas were detected at one of the flare headers, leading to further investigation on the relief sources. The investigation results determined that the refinery was using a significant amount of hydrogen in its flare system which was resulting in high heating values.

Figure 8:
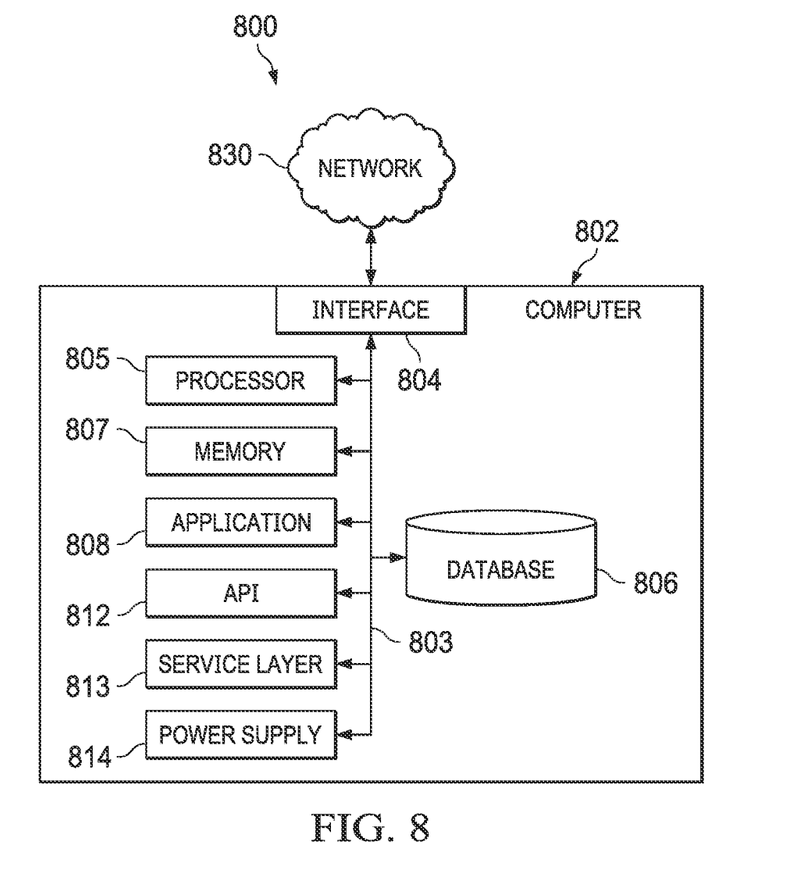
FIG. 8 is a block diagram illustrating an example computer system used to provide computational functionalities associated with described algorithms, methods, functions, processes, flows, and procedures as described in the present disclosure, according to some implementations of the present disclosure.

FIG. 8 is a block diagram of an example computer system 800 used to provide computational functionalities associated with described algorithms, methods, functions, processes, flows, and procedures described in the present disclosure, according to some implementations of the present disclosure. The illustrated computer 802 is intended to encompass any computing device such as a server, a desktop computer, a laptop/notebook computer, a wireless data port, a smart phone, a personal data assistant (PDA), a tablet computing device, or one or more processors within these devices, including physical instances, virtual instances, or both. The computer 802 can include input devices such as keypads, keyboards, and touch screens that can accept user information. Also, the computer 802 can include output devices that can convey information associated with the operation of the computer 802. The information can include digital data, visual data, audio information, or a combination of information. The information can be presented in a graphical user interface (UI) (or GUI).

The computer 802 can serve in a role as a client, a network component, a server, a database, a persistency, or components of a computer system for performing the subject matter described in the present disclosure. The illustrated computer 802 is communicably coupled with a network 830. In some implementations, one or more components of the computer 802 can be configured to operate within different environments, including cloud-computing-based environments, local environments, global environments, and combinations of environments.

At a top level, the computer 802 is an electronic computing device operable to receive, transmit, process, store, and manage data and information associated with the described subject matter. According to some implementations, the computer 802 can also include, or be communicably coupled with, an application server, an email server, a web server, a caching server, a streaming data server, or a combination of servers.

The computer 802 can receive requests over network 830 from a client application (for example, executing on another computer 802). The computer 802 can respond to the received requests by processing the received requests using software applications. Requests can also be sent to the computer 802 from internal users (for example, from a command console), external (or third) parties, automated applications, entities, individuals, systems, and computers.

Each of the components of the computer 802 can communicate using a system bus 803. In some implementations, any or all of the components of the computer 802, including hardware or software components, can interface with each other or the interface 804 (or a combination of both) over the system bus 803. Interfaces can use an application programming interface (API) 812, a service layer 813, or a combination of the API 812 and service layer 813. The API 812 can include specifications for routines, data structures, and object classes. The API 812 can be either computer-language independent or dependent. The API 812 can refer to a complete interface, a single function, or a set of APIs.

The service layer 813 can provide software services to the computer 802 and other components (whether illustrated or not) that are communicably coupled to the computer 802. The functionality of the computer 802 can be accessible for all service consumers using this service layer. Software services, such as those provided by the service layer 813, can provide reusable, defined functionalities through a defined interface. For example, the interface can be software written in JAVA, C++, or a language providing data in extensible markup language (XML) format. While illustrated as an integrated component of the computer 802, in alternative implementations, the API 812 or the service layer 813 can be stand-alone components in relation to other components of the computer 802 and other components communicably coupled to the computer 802. Moreover, any or all parts of the API 812 or the service layer 813 can be implemented as child or sub-modules of another software module, enterprise application, or hardware module without departing from the scope of the present disclosure.

The computer 802 includes an interface 804. Although illustrated as a single interface 804 in FIG. 8, two or more interfaces 804 can be used according to particular needs, desires, or particular implementations of the computer 802 and the described functionality. The interface 804 can be used by the computer 802 for communicating with other systems that are connected to the network 830 (whether illustrated or not) in a distributed environment. Generally, the interface 804 can include, or be implemented using, logic encoded in software or hardware (or a combination of software and hardware) operable to communicate with the network 830. More specifically, the interface 804 can include software supporting one or more communication protocols associated with communications. As such, the network 830 or the interface's hardware can be operable to communicate physical signals within and outside of the illustrated computer 802.

The computer 802 includes a processor 805. Although illustrated as a single processor 805 in FIG. 8, two or more processors 805 can be used according to particular needs, desires, or particular implementations of the computer 802 and the described functionality. Generally, the processor 805 can execute instructions and can manipulate data to perform the operations of the computer 802, including operations using algorithms, methods, functions, processes, flows, and procedures as described in the present disclosure.

The computer 802 also includes a database 806 that can hold data for the computer 802 and other components connected to the network 830 (whether illustrated or not). For example, database 806 can be an in-memory, conventional, or a database storing data consistent with the present disclosure. In some implementations, database 806 can be a combination of two or more different database types (for example, hybrid in-memory and conventional databases) according to particular needs, desires, or particular implementations of the computer 802 and the described functionality. Although illustrated as a single database 806 in FIG. 8, two or more databases (of the same, different, or combination of types) can be used according to particular needs, desires, or particular implementations of the computer 802 and the described functionality. While database 806 is illustrated as an internal component of the computer 802, in alternative implementations, database 806 can be external to the computer 802.

The computer 802 also includes a memory 807 that can hold data for the computer 802 or a combination of components connected to the network 830 (whether illustrated or not). Memory 807 can store any data consistent with the present disclosure. In some implementations, memory 807 can be a combination of two or more different types of memory (for example, a combination of semiconductor and magnetic storage) according to particular needs, desires, or particular implementations of the computer 802 and the described functionality. Although illustrated as a single memory 807 in FIG. 8, two or more memories 807 (of the same, different, or combination of types) can be used according to particular needs, desires, or particular implementations of the computer 802 and the described functionality. While memory 807 is illustrated as an internal component of the computer 802, in alternative implementations, memory 807 can be external to the computer 802.

The application 808 can be an algorithmic software engine providing functionality according to particular needs, desires, or particular implementations of the computer 802 and the described functionality. For example, application 808 can serve as one or more components, modules, or applications. Further, although illustrated as a single application 808, the application 808 can be implemented as multiple applications 808 on the computer 802. In addition, although illustrated as internal to the computer 802, in alternative implementations, the application 808 can be external to the computer 802.

The computer 802 can also include a power supply 814. The power supply 814 can include a rechargeable or non-rechargeable battery that can be configured to be either user- or non-user-replaceable. In some implementations, the power supply 814 can include power-conversion and management circuits, including recharging, standby, and power management functionalities. In some implementations, the power-supply 814 can include a power plug to allow the computer 802 to be plugged into a wall socket or a power source to, for example, power the computer 802 or recharge a rechargeable battery.

There can be any number of computers 802 associated with, or external to, a computer system containing computer 802, with each computer 802 communicating over network 830. Further, the terms "client," "user," and other appropriate terminology can be used interchangeably, as appropriate, without departing from the scope of the present disclosure. Moreover, the present disclosure contemplates that many users can use one computer 802 and one user can use multiple computers 802.

Described implementations of the subject matter can include one or more features, alone or in combination.

For example, in a first implementation, a computer-implemented method includes the following. Instantaneous flaring flowrate data is received from flaring sources of a flare network of a processing facility. The instantaneous flaring flowrate data is analyzed in conjunction with physical properties of relief sources obtained from a heat and material balance of the processing facility. A heating value and a molecular weight are determined for each relief source and flare header using a processing model associated with a relief source type, size, and identifications. The relief sources are connected using a data signal received and processed using the processing model. Reports are generated showing average daily heating values and molecular weights for each flare header. A real-time display is provided for monitoring instantaneous heating values and molecular weights for each flare header on a real-time basis.

The foregoing and other described implementations can each, optionally, include one or more of the following features:

A first feature, combinable with any of the following features, where analyzing the instantaneous flaring flowrate data includes using a data flow network of tables, views and scripts that are further stored in a data historian model operable to store into memory: parameters of flare-through elements concerning a relationship between generated data signals and a quantitative heating value and a molecular weight at each relief source; data associated with a heating value and a molecular weight of the flare header; and data associated with a heating value and a molecular weight for each plant.

A second feature, combinable with any of the previous or following features, where generating reports includes identifying whether particular flaring events are of a routine or non-routine nature, a flared volume, and a contribution of flare-through elements to the flared volume.

A third feature, combinable with any of the previous or following features, where providing the real-time display includes displaying, for each flare header, heating values over time.

A fourth feature, combinable with any of the previous or following features, where providing the real-time display include displaying, for each flare header, total emissions, $CO_2$ emissions, molecular weights, and a heating value.

A fifth feature, combinable with any of the previous or following features, where providing the real-time display includes displaying, for each flare header, a graph showing significant fluctuations in readings relative to a time period.

A sixth feature, combinable with any of the previous or following features, where determining the heating value and the molecular weight for each relief source and flare header includes generating one or more heating value graphs and molecular weight graphs displaying values over time.

In a second implementation, a non-transitory, computer-readable medium stores one or more instructions executable by a computer system to perform operations including the following. Instantaneous flaring flowrate data is received from flaring sources of a flare network of a processing facility. The instantaneous flaring flowrate data is analyzed in conjunction with physical properties of relief sources obtained from a heat and material balance of the processing facility. A heating value and a molecular weight are determined for each relief source and flare header using a processing model associated with a relief source type, size, and identifications. The relief sources are connected using a data signal received and processed using the processing model. Reports are generated showing average daily heating values and molecular weights for each flare header. A real-time display is provided for monitoring instantaneous heating values and molecular weights for each flare header on a real-time basis.

The foregoing and other described implementations can each, optionally, include one or more of the following features:

A first feature, combinable with any of the following features, where analyzing the instantaneous flaring flowrate data includes using a data flow network of tables, views and scripts that are further stored in a data historian model operable to store into memory: parameters of flare-through elements concerning a relationship between generated data signals and a quantitative heating value and a molecular weight at each relief source; data associated with a heating value and a molecular weight of the flare header; and data associated with a heating value and a molecular weight for each plant.

A second feature, combinable with any of the previous or following features, where generating reports includes identifying whether particular flaring events are of a routine or non-routine nature, a flared volume, and a contribution of flare-through elements to the flared volume.

A third feature, combinable with any of the previous or following features, where providing the real-time display includes displaying, for each flare header, heating values over time.

A fourth feature, combinable with any of the previous or following features, where providing the real-time display include displaying, for each flare header, total emissions, $CO_2$ emissions, molecular weights, and a heating value.

A fifth feature, combinable with any of the previous or following features, where providing the real-time display includes displaying, for each flare header, a graph showing significant fluctuations in readings relative to a time period.

A sixth feature, combinable with any of the previous or following features, where determining the heating value and the molecular weight for each relief source and flare header includes generating one or more heating value graphs and molecular weight graphs displaying values over time.

In a third implementation, a computer-implemented system includes one or more processors and a non-transitory computer-readable storage medium coupled to the one or more processors and storing programming instructions for execution by the one or more processors. The programming instructions instruct the one or more processors to perform operations including the following. Instantaneous flaring flowrate data is received from flaring sources of a flare network of a processing facility. The instantaneous flaring flowrate data is analyzed in conjunction with physical properties of relief sources obtained from a heat and material balance of the processing facility. A heating value and a molecular weight are determined for each relief source and flare header using a processing model associated with a relief source type, size, and identifications. The relief sources are connected using a data signal received and processed using the processing model. Reports are generated showing average daily heating values and molecular weights for each flare header. A real-time display is provided for monitoring instantaneous heating values and molecular weights for each flare header on a real-time basis.

The foregoing and other described implementations can each, optionally, include one or more of the following features:

A first feature, combinable with any of the following features, where analyzing the instantaneous flaring flowrate data includes using a data flow network of tables, views and scripts that are further stored in a data historian model operable to store into memory: parameters of flare-through elements concerning a relationship between generated data signals and a quantitative heating value and a molecular weight at each relief source; data associated with a heating value and a molecular weight of the flare header; and data associated with a heating value and a molecular weight for each plant.

A second feature, combinable with any of the previous or following features, where generating reports includes identifying whether particular flaring events are of a routine or non-routine nature, a flared volume, and a contribution of flare-through elements to the flared volume.

A third feature, combinable with any of the previous or following features, where providing the real-time display includes displaying, for each flare header, heating values over time.

A fourth feature, combinable with any of the previous or following features, where providing the real-time display include displaying, for each flare header, total emissions, $CO_2$ emissions, molecular weights, and a heating value.

A fifth feature, combinable with any of the previous or following features, where providing the real-time display includes displaying, for each flare header, a graph showing significant fluctuations in readings relative to a time period.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs. Each computer program can include one or more modules of computer program instructions encoded on a tangible, non-transitory, computer-readable computer-storage medium for execution by, or to control the operation of, data processing apparatus. Alternatively, or additionally, the program instructions can be encoded in/on an artificially generated propagated signal. For example, the signal can be a machine-generated electrical, optical, or electromagnetic signal that is generated to encode information for transmission to a suitable receiver apparatus for execution by a data processing apparatus. The computer-storage medium can be a machine-readable storage device, a machine-readable storage substrate, a random or serial access memory device, or a combination of computer-storage mediums.

The terms "data processing apparatus," "computer," and "electronic computer device" (or equivalent as understood by one of ordinary skill in the art) refer to data processing hardware. For example, a data processing apparatus can encompass all kinds of apparatuses, devices, and machines for processing data, including by way of example, a programmable processor, a computer, or multiple processors or computers. The apparatus can also include special purpose logic circuitry including, for example, a central processing unit (CPU), a field-programmable gate array (FPGA), or an application-specific integrated circuit (ASIC). In some implementations, the data processing apparatus or special purpose logic circuitry (or a combination of the data processing apparatus or special purpose logic circuitry) can be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with or without conventional operating systems, such as LINUX, UNIX, WINDOWS, MAC OS, ANDROID, or IOS.

A computer program, which can also be referred to or described as a program, software, a software application, a module, a software module, a script, or code, can be written in any form of programming language. Programming languages can include, for example, compiled languages, interpreted languages, declarative languages, or procedural languages. Programs can be deployed in any form, including as stand-alone programs, modules, components, subroutines, or units for use in a computing environment. A computer program can, but need not, correspond to a file in a file system. A program can be stored in a portion of a file that holds other programs or data, for example, one or more scripts stored in a markup language document, in a single file dedicated to the program in question, or in multiple coordinated files storing one or more modules, sub-programs, or portions of code. A computer program can be deployed for execution on one computer or on multiple computers that are located, for example, at one site or distributed across multiple sites that are interconnected by a communication network. While portions of the programs illustrated in the various figures may be shown as individual modules that implement the various features and functionality through various objects, methods, or processes, the programs can instead include a number of sub-modules, third-party services, components, and libraries. Conversely, the features and functionality of various components can be combined into single components as appropriate. Thresholds used to make computational determinations can be statically, dynamically, or both statically and dynamically determined.

The methods, processes, or logic flows described in this specification can be performed by one or more programmable computers executing one or more computer programs to perform functions by operating on input data and generating output. The methods, processes, or logic flows can also be performed by, and apparatus can also be implemented as, special purpose logic circuitry, for example, a CPU, an FPGA, or an ASIC.

Computers suitable for the execution of a computer program can be based on one or more of general and special purpose microprocessors and other kinds of CPUs. The elements of a computer are a CPU for performing or executing instructions and one or more memory devices for storing instructions and data. Generally, a CPU can receive instructions and data from (and write data to) a memory.

Graphics processing units (GPUs) can also be used in combination with CPUs. The GPUs can provide specialized processing that occurs in parallel to processing performed by CPUs. The specialized processing can include artificial intelligence (AI) applications and processing, for example. GPUs can be used in GPU clusters or in multi-GPU computing.

A computer can include, or be operatively coupled to, one or more mass storage devices for storing data. In some implementations, a computer can receive data from, and transfer data to, the mass storage devices including, for example, magnetic, magneto-optical disks, or optical disks. Moreover, a computer can be embedded in another device, for example, a mobile telephone, a personal digital assistant (PDA), a mobile audio or video player, a game console, a global positioning system (GPS) receiver, or a portable storage device such as a universal serial bus (USB) flash drive.

Computer-readable media (transitory or non-transitory, as appropriate) suitable for storing computer program instructions and data can include all forms of permanent/non-permanent and volatile/non-volatile memory, media, and memory devices. Computer-readable media can include, for example, semiconductor memory devices such as random access memory (RAM), read-only memory (ROM), phase change memory (PRAM), static random access memory (SRAM), dynamic random access memory (DRAM), erasable programmable read-only memory (EPROM), electrically erasable programmable read-only memory (EEPROM), and flash memory devices. Computer-readable media can also include, for example, magnetic devices such as tape, cartridges, cassettes, and internal/removable disks. Computer-readable media can also include magneto-optical disks and optical memory devices and technologies including, for example, digital video disc (DVD), CD-ROM, DVD+/−R, DVD-RAM, DVD-ROM, HD-DVD, and BLU-RAY. The memory can store various objects or data, including caches, classes, frameworks, applications, modules, backup data, jobs, web pages, web page templates, data structures, database tables, repositories, and dynamic information. Types of objects and data stored in memory can include parameters, variables, algorithms, instructions, rules, constraints, and references. Additionally, the memory can include logs, policies, security or access data, and reporting files. The processor and the memory can be supplemented by, or incorporated into, special purpose logic circuitry.

Implementations of the subject matter described in the present disclosure can be implemented on a computer having a display device for providing interaction with a user, including displaying information to (and receiving input from) the user. Types of display devices can include, for example, a cathode ray tube (CRT), a liquid crystal display (LCD), a light-emitting diode (LED), and a plasma monitor. Display devices can include a keyboard and pointing devices including, for example, a mouse, a trackball, or a trackpad. User input can also be provided to the computer through the use of a touchscreen, such as a tablet computer surface with pressure sensitivity or a multi-touch screen using capacitive or electric sensing. Other kinds of devices can be used to provide for interaction with a user, including to receive user feedback including, for example, sensory feedback including visual feedback, auditory feedback, or tactile feedback. Input from the user can be received in the form of acoustic, speech, or tactile input. In addition, a computer can interact with a user by sending documents to, and receiving documents from, a device that the user uses. For example, the computer can send web pages to a web browser on a user's client device in response to requests received from the web browser.

The term "graphical user interface," or "GUI," can be used in the singular or the plural to describe one or more graphical user interfaces and each of the displays of a particular graphical user interface. Therefore, a GUI can represent any graphical user interface, including, but not limited to, a web browser, a touch-screen, or a command line interface (CLI) that processes information and efficiently presents the information results to the user. In general, a GUI can include a plurality of user interface (UI) elements, some or all associated with a web browser, such as interactive fields, pull-down lists, and buttons. These and other UI elements can be related to or represent the functions of the web browser.

Implementations of the subject matter described in this specification can be implemented in a computing system that includes a back-end component, for example, as a data server, or that includes a middleware component, for example, an application server. Moreover, the computing system can include a front-end component, for example, a client computer having one or both of a graphical user interface or a Web browser through which a user can interact with the computer. The components of the system can be interconnected by any form or medium of wireline or wireless digital data communication (or a combination of data communication) in a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) (for example, using 802.11 a/b/g/n or 802.20 or a combination of protocols), all or a portion of the Internet, or any other communication system or systems at one or more locations (or a combination of communication networks). The network can communicate with, for example, Internet Protocol (IP) packets, frame relay frames, asynchronous transfer mode (ATM) cells, voice, video, data, or a combination of communication types between network addresses.

The computing system can include clients and servers. A client and server can generally be remote from each other and can typically interact through a communication network. The relationship of client and server can arise by virtue of computer programs running on the respective computers and having a client-server relationship.

Cluster file systems can be any file system type accessible from multiple servers for read and update. Locking or consistency tracking may not be necessary since the locking of exchange file system can be done at application layer. Furthermore, Unicode data files can be different from non-Unicode data files.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations. It should be understood that the described program components and systems can generally be integrated together in a single software product or packaged into multiple software products.

Accordingly, the previously described example implementations do not define or constrain the present disclosure. Other changes, substitutions, and alterations are also possible without departing from the spirit and scope of the present disclosure.

Furthermore, any claimed implementation is considered to be applicable to at least a computer-implemented method; a non-transitory, computer-readable medium storing computer-readable instructions to perform the computer-implemented method; and a computer system including a computer memory interoperably coupled with a hardware processor configured to perform the computer-implemented method or the instructions stored on the non-transitory, computer-readable medium.

What is claimed is:

1. A computer-implemented method, comprising:
   receiving instantaneous flaring flowrate data from flaring sources of a flare network of a processing facility;
   analyzing the instantaneous flaring flowrate data in conjunction with the physical properties of relief sources obtained from a heat and material balance of the processing facility;
   determining, using a processing model associated with a relief source type, size, and identifications, a heating value and a molecular weight for each relief source and flare header, wherein the relief sources are connected using a data signal received and processed using the processing model;
   generating reports showing average daily heating values and molecular weights for each flare header; and
   providing a real-time display to monitor instantaneous heating values and molecular weights for each flare header on a real-time basis.

2. The computer-implemented method of claim 1, wherein analyzing the instantaneous flaring flowrate data includes using a data flow network of tables, views and scripts that are further stored in a data historian model operable to store into memory:
   parameters of flare-through elements concerning a relationship between generated data signals and a quantitative heating value and a molecular weight at each relief source;
   data associated with a heating value and a molecular weight of the flare header; and
   data associated with a heating value and a molecular weight for each plant.

3. The computer-implemented method of claim 1, wherein generating reports includes identifying whether particular flaring events are of a routine or non-routine nature, a flared volume, and a contribution of flare-through elements to the flared volume.

4. The computer-implemented method of claim 1, wherein providing the real-time display includes displaying, for each flare header, heating values over time.

5. The computer-implemented method of claim 1, wherein providing the real-time display include displaying, for each flare header, total emissions, $CO_2$ emissions, molecular weights, and a heating value.

6. The computer-implemented method of claim 1, wherein providing the real-time display includes displaying, for each flare header, a graph showing significant fluctuations in readings relative to a time period.

7. The computer-implemented method of claim 1, wherein determining the heating value and the molecular weight for each relief source and flare header includes generating one or more heating value graphs and molecular weight graphs displaying values over time.

8. A non-transitory, computer-readable medium storing one or more instructions executable by a computer system to perform operations comprising:
   receiving instantaneous flaring flowrate data from flaring sources of a flare network of a processing facility;
   analyzing the instantaneous flaring flowrate data in conjunction with the physical properties of relief sources obtained from a heat and material balance of the processing facility;
   determining, using a processing model associated with a relief source type, size, and identifications, a heating value and a molecular weight for each relief source and flare header, wherein the relief sources are connected using a data signal received and processed using the processing model;
   generating reports showing average daily heating values and molecular weights for each flare header; and
   providing a real-time display to monitor instantaneous heating values and molecular weights for each flare header on a real-time basis.

9. The non-transitory, computer-readable medium of claim 8, wherein analyzing the instantaneous flaring flowrate data includes using a data flow network of tables, views and scripts that are further stored in a data historian model operable to store into memory:

parameters of flare-through elements concerning a relationship between generated data signals and a quantitative heating value and a molecular weight at each relief source;

data associated with a heating value and a molecular weight of the flare header; and data associated with a heating value and a molecular weight for each plant.

10. The non-transitory, computer-readable medium of claim 8, wherein generating reports includes identifying whether particular flaring events are of a routine or non-routine nature, a flared volume, and a contribution of flare-through elements to the flared volume.

11. The non-transitory, computer-readable medium of claim 8, wherein providing the real-time display includes displaying, for each flare header, heating values over time.

12. The non-transitory, computer-readable medium of claim 8, wherein providing the real-time display include displaying, for each flare header, total emissions, $CO_2$ emissions, molecular weights, and a heating value.

13. The non-transitory, computer-readable medium of claim 8, wherein providing the real-time display includes displaying, for each flare header, a graph showing significant fluctuations in readings relative to a time period.

14. The non-transitory, computer-readable medium of claim 8, wherein determining the heating value and the molecular weight for each relief source and flare header includes generating one or more heating value graphs and molecular weight graphs displaying values over time.

15. A computer-implemented system, comprising:
one or more processors; and
a non-transitory computer-readable storage medium coupled to the one or more processors and storing programming instructions for execution by the one or more processors, the programming instructions instructing the one or more processors to perform operations comprising:
receiving instantaneous flaring flowrate data from flaring sources of a flare network of a processing facility;
analyzing the instantaneous flaring flowrate data in conjunction with the physical properties of relief sources obtained from a heat and material balance of the processing facility;
determining, using a processing model associated with a relief source type, size, and identifications, a heating value and a molecular weight for each relief source and flare header, wherein the relief sources are connected using a data signal received and processed using the processing model;
generating reports showing average daily heating values and molecular weights for each flare header; and
providing a real-time display to monitor instantaneous heating values and molecular weights for each flare header on a real-time basis.

16. The computer-implemented system of claim 15, wherein analyzing the instantaneous flaring flowrate data includes using a data flow network of tables, views and scripts that are further stored in a data historian model operable to store into memory:
parameters of flare-through elements concerning a relationship between generated data signals and a quantitative heating value and a molecular weight at each relief source;
data associated with a heating value and a molecular weight of the flare header; and
data associated with a heating value and a molecular weight for each plant.

17. The computer-implemented system of claim 15, wherein generating reports includes identifying whether particular flaring events are of a routine or non-routine nature, a flared volume, and a contribution of flare-through elements to the flared volume.

18. The computer-implemented system of claim 15, wherein providing the real-time display includes displaying, for each flare header, heating values over time.

19. The computer-implemented system of claim 15, wherein providing the real-time display include displaying, for each flare header, total emissions, $CO_2$ emissions, molecular weights, and a heating value.

20. The computer-implemented system of claim 15, wherein providing the real-time display includes displaying, for each flare header, a graph showing significant fluctuations in readings relative to a time period.

* * * * *